(12) United States Patent
Tian et al.

(10) Patent No.: US 6,599,330 B2
(45) Date of Patent: Jul. 29, 2003

(54) METHOD FOR COLORING HAIR WITH REMOVABLE HAIR COLOR

(75) Inventors: Minmin Tian, East Brunswick, NJ (US); Geoffrey Robert Hawkins, Langhorne, PA (US); Alexander C. Chan, Cranbury, NJ (US)

(73) Assignee: Revlon Consumer Products Corporation, New York, NY (US)

( * ) Notice: Subject to any disclaimer, the term of this patent is extended or adjusted under 35 U.S.C. 154(b) by 0 days.

(21) Appl. No.: 10/245,160

(22) Filed: Nov. 4, 2002

(65) Prior Publication Data

US 2003/0106168 A1 Jun. 12, 2003

Related U.S. Application Data

(63) Continuation of application No. 09/522,543, filed on Mar. 10, 2000, now abandoned.

(51) Int. Cl.[7] .................................................. A61K 7/13
(52) U.S. Cl. ....................... 8/405; 8/428; 8/431; 8/432; 8/435
(58) Field of Search ............................ 8/405, 428, 431, 8/432, 435

(56) References Cited

U.S. PATENT DOCUMENTS

| | | | |
|---|---|---|---|
| 5,340,367 A | 8/1994 | Schultz | 8/432 |
| 6,040,005 A | 3/2000 | Carr | 427/197 |
| 6,106,579 A | 8/2000 | Kunz | 8/432 |
| 6,171,347 B1 | 1/2001 | Kunz | 8/407 |
| 6,241,784 B1 | 6/2001 | De La Mettrie | 8/406 |
| 6,251,145 B1 * | 6/2001 | De La Mettrie et al. | 8/405 |
| 6,361,767 B1 | 3/2002 | Malle | 424/70.1 |

* cited by examiner

Primary Examiner—Charles Boyer
Assistant Examiner—Eisa Elhilo
(74) Attorney, Agent, or Firm—Julie Blackburn

(57) ABSTRACT

A method for coloring hair and removing the color from the hair when desired, comprising coloring the hair with an aqueous hair color composition comprising, in combination: (i) a reducing agent capable of reducing the —S—S— bonds on the hair fiber surface to form reactive —SH groups; and (ii) a dye molecule containing chemical groups reactive with the —SH groups on the hair fiber surface to form —S—S— bonds between the dye molecule and the hair fiber surface when the hair color composition is applied to the hair at ambient conditions; wearing the colored hair for the desired period of time; and then removing the color from the hair by contacting the hair with an aqueous based color removal composition containing a reducing agent capable of disrupting the —S—S— bonds between the dye molecule and the hair fiber surface to cause the dye molecule to become disassociated from the hair fiber; and a method for removing dye bonded to the hair fibers via an —S—S— linkage, comprising applying to the hair an aqueous based color removal composition containing a reducing agent capable of disrupting the —S—S— bonds between the dye and hair fiber surface.

20 Claims, No Drawings

METHOD FOR COLORING HAIR WITH REMOVABLE HAIR COLOR

RELATED APPLICATION

This application is a continuation of U.S. patent application Ser. No. 09/522,543, filed Mar. 10, 2000 abandoned.

TECHNICAL FIELD

The invention is in the field of coloring hair with hair dye compositions.

BACKGROUND OF THE INVENTION

At one time or another, most individuals have been interested in coloring their hair. An individual's concern about how the color will look on them, and the inability to quickly change bad color results, is one common deterrent to experimentation with hair color.

Commercially available hair color generally falls into one of three categories: permanent, semi-permanent, or temporary.

The term "permanent" generally refers to oxidative dyes, which provide hair color that lasts about four to six weeks. Oxidative hair dyes are usually sold in the form of a two component kit. In one container is an aqueous alkaline composition in the liquid, gel, or crème form that contains oxidative dyes in addition to other ingredients. In the other container is a developer composition that contains an oxidizing agent, usually hydrogen peroxide. The two components are mixed immediately prior to use and applied to hair. The peroxide in the composition causes the hair shaft to swell, permitting the dye precursors in the lotion to penetrate the hair shaft. The oxidizing agent then oxidizes the dye precursors, which then combine to form large color molecules within the hair shaft. The mixture is left on the hair for an appropriate period of time, generally 20 to 60 minutes, then rinsed off with water. Oxidative dyes provide the most long lasting color because the dye molecules polymerize within the hair shaft. However, the oxidizing agents necessary to the process sometimes cause undesirable effects on sensitive hair. Some consumers with sensitive hair note that prolonged use of oxidizing agents may cause dry, brittle, overprocessed hair.

It is known in the art that oxidative hair color can be removed from the hair by applying to the hair an aqueous composition containing an oxidizing agent. However, the color removal is very inconsistent, and the oxidizing agents are prone to causing further damage to the hair.

Semi-permanent hair color differs from oxidative color because the dye molecules are preformed prior to application to the hair, and the size of the molecules does not change during the dye process. These molecules tend to deposit on the surface of the hair, rather than penetrating the hair shaft. Semi-permanent hair color is perceived to be gentler to hair because peroxide is not used, and the dye molecules deposited on the hair surface do not affect the integrity of the hair shaft. Unfortunately, semi-permanent hair color only remains on the hair through six to twelve shampoos.

As with oxidative color, semi-permanent color may be removed from the hair by application of an aqueous based composition containing an oxidizing agent, however with the same drawbacks.

Temporary hair color is applied to the hair much in the manner of a superficial coating. It is generally removable with shampooing. Temporary hair color is most often used when a unique effect is desired for a very short period of time. An example of temporary haircolor is "hairscara", which is a colored mixture that can be dabbed onto the hair with a brush much like makeup is applied to the skin. Like makeup, hairscara is removed when the hair is washed.

The gold standard for hair color is a color that does not utilize peroxide or similar oxidizing agents, is as gentle to hair as semi-permanent color, yet provides the permanence see with oxidative color, but at the same time can be removed from the hair when desired with a simple process and composition that does not damage the hair.

It is an object of the invention to provide a method for coloring hair with a hair color composition that will color hair to the same degree as permanent hair color but can be removed from the hair when desired.

It is an object of the invention to provide a method for coloring hair with a hair color composition that will color hair to the same degree as permanent haircolor, but can be removed from the hair when desired.

It is an object of the invention to provide a method for coloring hair with a hair color composition that does not utilize oxidizing agents, or utilizes them in very small amounts.

It is another object of the invention to provide a method for coloring hair with a hair color composition that provides the same degree of gentleness as found in semi-permanent hair color, yet provides the relative permanence found with oxidative hair color, which color can be removed from the hair when desired in a simple one-step process.

SUMMARY OF THE INVENTION

A method for coloring hair and removing the color from the hair when desired, comprising the steps of:

(a) coloring the hair with an aqueous hair color composition comprising, in combination: (i) a reducing agent capable of reducing the —S—S— bonds on the hair fiber surface to form reactive —SH groups and (ii) a dye molecule containing chemical groups reactive with the —SH groups on the hair fiber surface to form —S—S— bonds between the dye molecule and the hair fiber surface when the hair color composition is applied to the hair at ambient conditions;

(b) wearing the colored hair for the desired period of time;

(c) removing the color applied in step (a) from the hair by contacting the hair with an aqueous based composition containing a reducing agent capable of disrupting the —S—S— bonds between the dye molecule and the hair fiber surface to cause the dye molecule to become disassociated from the hair fiber.

The invention further comprises a method for removing a dye molecule bonded to the hair fibers via an —S—S— linkage, comprising applying to the hair an aqueous based composition containing a reducing agent capable of disrupting the —S—S— bonds between the dye molecule and the hair fiber surface.

DETAILED DESCRIPTION

The invention comprises a method for coloring hair and removing the color from the hair when desired. The ability to achieve this result is dependent upon the interaction between a hair color composition containing a reducing agent and specific dye molecules having reactive groups capable of bonding with similar reactive groups formed on the hair fiber surface by the reducing agent; and a removal composition that contains specific ingredients that are capable of disrupting the bond formed between the reactive groups of dye molecule and the hair fiber. In particular, the hair fiber contains disulfide bonds, generally referred to as K—S—S—K' where K and K' refer to hair keratin, and S is sulfur. In the method of the invention, the reducing agent found in the hair color composition will cause the K—S—S—K' bonds to cleave and form K—S—H and H—S—K' bonds. The dye molecule, which contains free chemical groups reactive with the —S—H groups on the hair fiber surface, will react with these —SH groups and, at ambient conditions, the oxygen in the air will cause the disulfide bonds to reform between the dye molecule and the hair fiber surface, such that the dye molecule is bonded to the hair fiber surface in a manner that can be depicted below (where K and S are as above defined).

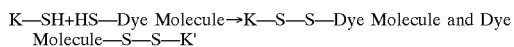

K—SH+HS—Dye Molecule→K—S—S—Dye Molecule and Dye Molecule—S—S—K'

The hair color composition and the reducing agent composition, and related method will be further described below, with all percentages mentioned herein being percentages by weight unless otherwise indicated.

I. The Hair Color Composition

The hair color composition used in the method of the invention is preferably an aqueous based composition containing the reducing agent and the dye molecule in aqueous media, and, if desired, ancillary ingredients that improve the aesthetics of the composition.

A. The Dye Molecule

The hair color composition used in the method of the invention comprises a dye molecule that contains a chromophore, and at least one free reactive group which, upon contact with hair, reacts with the —SH groups on the hair fiber surface which may be formed by the reducing agent, to form an —S—S— bond between the dye molecule and the hair fiber surface. The —S—S— bond between the dye molecule and the hair fiber surface is capable of causing the dye molecule to remain affixed or "locked" to the hair fiber surface for so long as the wearer desires, but certainly long enough to be considered "permanent" hair color in terms of the four to six week longevity typically associated with current permanent haircolor. Similarly, when desired, the user may remove the hair color by applying a reducing agent composition that disrupts the —S—S— bonds formed between the dye molecule and the hair fiber surface, the "key" that "unlocks" the dye from the hair and restoring the hair to its original color. Both the hair color composition and the reducing agent composition are gentle to the hair and do not cause the undesirable effects sometimes noted with use of oxidative systems.

The term "chemical groups reactive with the —SH group" when referring to the dye molecule, means groups such as —SH, thiouronium salts, bunte salts, and the like which, when found on the dye molecule, react with the free —SH groups formed on the hair fiber surface by the reducing agent, to form an —S—S— bond between the dye molecule and the hair fiber surface at ambient conditions. In particular, air oxidation will assist in reformation of the —S—S— bond between the dye molecule and the hair fiber surface.

Any chromophore is suitable for use in dye molecule used in the method of the invention, provided it is capable of imparting color to the hair fiber.

The dye molecules may be present in the form of complex molecules or polymers, or may simply be a chromophore compound which is substituted with the requisite —SH group or protected —SH groups as are found in Bunte or isothiouronium salts.

Preferably, the hair color composition comprises 0.1–95%, preferably 0.5–85%, more preferably 1–75% by weight of the total composition of the dye molecule.

1. Substituted Chromophore

The dye molecule may simply be a chromophore that is substituted with one or more —SH groups. Any chromophore which provides color to the hair is suitable for use, provided it has been derivatized such that it contains at least one free —SH group. Suitable compounds include Acid dyes, Basic dyes, Disperse dyes, and HC dyes, as well as dyes typically used for oxidative dyeing of the hair such as aminophenols, nitrophenols, and the like; which are derivatized by substituting on the compound on or more —SH groups. Compounds suitable for use, after derivatization, are set forth in the International Cosmetic Ingredient Dictionary and Handbook, Eighth Edition, 2000, under the heading "Color Additives—Hair", beginning at page 1666 through 1668, which is hereby incorporated by reference. The mentioned compounds may be modified to include —SH groups by.

2. Polymers

The dye molecule may be in the form of a polymer, having one or more repeating units that are the same or different, i.e. a homopolymer, copolymer, terpolymer, or graft or block polymers of unsaturated monomers such as acrylate, methacrylate, ethylene, propylene, styrene, α-methyl styrene, vinyl acetate carboxylic acid containing monomers such as acrylic acid or methacrylic acid, epoxy, and the like; wherein the dye molecule contains at least chemical group reactive with the —SH groups formed on the hair fiber surface by the reducing agent, to form an —S—S— bond, and a chromophore capable of coloring the hair. The placement of the chemical group reactive with the —SH group, and the chromophore within the polymeric dye molecule may vary. For example, the polymeric dye molecule may be a copolymer where these groups are attached to one repeating monomer, and the chromophore attached to another repeating monomer; or a copolymer where both the chemical group and the chromophore are attached to the same monomer and the other monomer in the copolymer remains unsubstituted. Or the polymeric dye molecule may be a homopolymer where the chemical group and the chromophore are attached to one or more of the identical repeating units. Generally, the chemical group and chromophore may be in any placement, provided the resulting polymeric dye molecule is capable of coloring hair and bonding to the hair via formation of —S—S— linkages at ambient conditions.

Preferred monomers for use in forming polymers used in the compositions of the invention are those having the following general formulas:

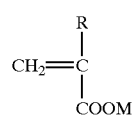

I.

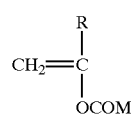

II.

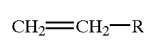

II.

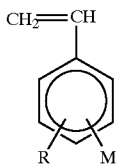

wherein:
R is H, $C_{1-6}$ alkyl, halogen, $C_{1-6}$ hydroxyalkyl, substituted or unsubstituted aminoalkyl; and
M is independently selected from:
(a) a substituted or unsubstituted $C_{1-30}$ straight or branched chain alkyl, where the substitutents are halogen or alkoxy; pyrrolidone; or a substituted or unsubstituted aromatic, cyclic, alicyclic, or bicyclic ring where the substitutents are $C_{1-30}$ straight or branched chain alkyl or halogen;
(b) $Z_nR'$, wherein Z is $CH_2$, and n is 1–20, and R' is SH, $NR''_3$, an isothiouronium salt, or Bunte salts with cationic moiety selected from ammonium, alkaline metal ions or earth alkaline metal ions, transition metal ions as $Li^+$, $Na^+$, $K^+$, $Mg^{2+}$, $Ca^{2+}$; $Al^{3+}$, $Zn^{2+}$, wherein R'' is H, $C_{1-6}$ alkyl, $C_{1-6}$ hydroxyalkyl, or substituted or unsubstituted aminoalkyl, or two or more R'' together form a substituted or unsubstituted heterocyclic 5 or 6 membered ring where the substitutents are selected from $C_{1-6}$ alkyl, $C_{1-6}$ hydroxyalkyl, or aminoalkyl; or
(c) X-D wherein X is a linking group which is preferably selected from:
—$C_mH_{2m}NR'$—, —NR'—, —NR'C=O—, —C(O)NR'—, —NR'SO_2$—, —SO_2NR'$—, —$C_mH_{2m}NR'CO_2$, or $C_mH_{2m}CO_2$;
wherein m is an integer from 0 to 1,000.
and D is a chromophore that absorbs visible light;
with the proviso that the polymer contains at least one —SH group and at least one X-D group.

Preferred polymers are those comprised of monomers

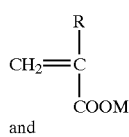

and

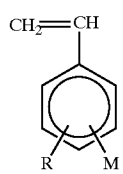

wherein:
each M is independently a $C_{1-6}$ straight or branched chain alkyl; $Z_nR'$ wherein Z is $CH_2$, R' is SH, or NR'' wherein R'' is a $C_{1-4}$ alkyl, and n is 1 to 4; or X-D wherein X is a linking group and D is a dye compound; and the polymer has at least one —SH group and at least one X-D group.

Particularly preferred polymers are comprised of monomers where M is $Z_nR'$ wherein Z is $CH_2$, n is 2, R' is SH or $NR''_3$; wherein R'' is as described above; or X-D wherein X and D are as described above.

Most preferred are polymers of the formula:

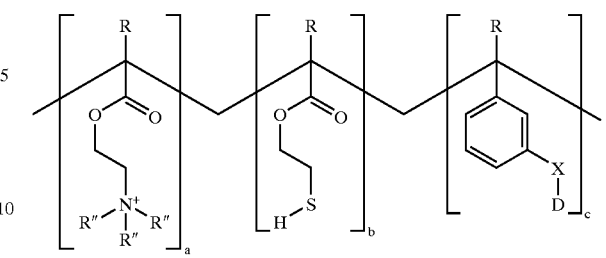

wherein:
n, y, and z are each independently integers ranging from 1 to 100,000;
Each R'' is independently H, or $C_{1-6}$ alkyl;
X is a linking group; and
D is a dye compound or chromophore that absorbs visible light.

The chromophore, D, that may be used is any chromophore that is suitable for use in dyeing hair or textile fibers, and which is capable of absorbing visible light, e.g. light in the fluorescent wavelength range. Examples of these chromophores include monoazo, diazo, polyazo dyes or metallic derivatives thereof, as well as those mentioned above with respect to the dye compound. Further preferred examples include anthroquinones, phthalocyanine, formazan, methine, azomethine, dioxazine, phenazine, stilbene, triphenylmethane, xanthene, thioxanthene, nitroaryl, naphthoquinone, pyrenequionone, and the like. Particularly preferred chromophores are monoazo chromophores.

The polymeric dye compounds used in the method of the invention may be made by either radical initiative polymerization or condensation polymerization of the above mentioned monomers in the standard manner according to methods well known in the art.

3. Complex Molecules

The dye molecule may be in the form of complex molecules formed by reacting one or more chemical compounds such as the chromophore, another compound containing the reactive chemical groups, chemical linking groups, and the like. Typically these complex molecules comprise a chromophore; and a linking group that attaches the chromophore to another chemical compound substituted with one or more of the requisite chemical groups. Such complex molecules may be represented by the general formula:

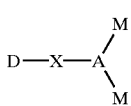

wherein D, X, and M are as defined above with respect to the polymer; and A is a chemical compound which is capable of substitution with one or more M groups. Preferably, A is a nitrogen containing heterocycle such as pyrimidine, triazine, pyridone, quinoxaline, or pyrimidone; with the proviso that at least one M is $Z_nR$, wherein Z is $CH_2$, and n is 1–20, and R is SH. Examples of such dye compounds are disclosed in PCT/WO patent applications 99/51195; 99/51688; and 99/51194; which are hereby incorporated by reference in their entirety.

B. The Reducing Agent

The hair color composition used in the method of the invention comprises a reducing agent that is capable of reacting with the disulfide bonds on the hair fiber surface to cause formation of —SH groups on the hair fiber surface. The term "reducing agent" means a compound that loses electrons when reacted with an oxidizing agent, and in most cases contributes hydrogen to other molecules. The reducing agent used in the hair color composition must be compatible with the dye molecule and the other ingredients in the hair color composition such that when the hair color composition is applied to the hair the reducing agent acts immediately to cause formation of —SH groups on the hair fiber surface, and, simultaneously, the chemical groups on the dye molecule that are reactive with the —SH groups formed by the reducing agent, are capable of reacting with these —SH groups at ambient conditions to form —S—S— bonds, thus causing the dye molecule to "lock" onto the hair. The amount of reducing agent in the hair color composition must be sufficient to cause formation of sufficient —SH groups on the hair fiber such that an adequate amount of the dye molecule can attach to the hair fiber surface by reaction between the chemical groups reactive with the —SH-groups. If the hair color composition does not contain sufficient reducing agent, the number of —SH groups formed on the hair fiber surface will not be sufficient to permit enough dye molecule to attach, and the hair will not be adequately colored. Suggested ranges of reducing agent for use in the hair color composition are 0.5–85%, 1–75%, more preferably 1.5–25% by weight of the total hair color composition.

A variety of reducing agents may be suitable for use in the hair color compositions of the invention, including, ammonium compounds such as ammonium bisulfite, sulfite, thioglycolate, or thiolactate; cysteamine hydrochloride, cysteine, cysteine hydrochloride, dithiothreitol, ethanolamine hydrochloride, glutathione, glyceryl thiopropionate, hydroquinone, isooctyl thioglycolate, glyceryl thioglycolate, magnesium thioglycolate, mercaptopropionic acid, potassium metabisulfite, potassium sulfite, potassium thioglycolate, sodium bisulfite, sodium hydrosulfite, sodium hydroxymethane sulfonate, sodium metabisulfite, sodium sulfite, sodium thioglycolate, strontium thioglycolate, thioglycolic acid, thiosalicyclic acid, and the like. The preferred reducing agents are glyceryl thioglycolate or thioglycolic acid.

C. Aqueous Carrier

The hair color composition is an aqueous based composition, which contains water in addition to the dye molecule and reducing agent. Generally, the hair color composition comprises 0.5–99%, preferably 1–90%, more preferably 3–75% by weight of the total composition of water.

D. Other Ingredients

The hair color compositions may also contain other ingredients that may improve the aesthetics of the formula, or provide other effects. Examples of other ingredients include humectants, pH adjusters, hair conditioning agents, biological products, and so forth.

1. Humectants

The hair color compositions may contain one or more humectants which are desirable because they tend to swell and moisturize the hair fiber. Suggested ranges of humectant include 0.1–30%, preferably 0.5–25%, more preferably 1–20% by weight of the total composition. Suitable humectants include sugars such as glucose, fructose, maltose, glycerin, glycol, mannitol, polyethylene glycols having from 4 to 800 repeating ethylene glycol units, alkoxylated polypropylene glycols either alone or substituted with fatty radicals, sorbitol, xylitol, xylose. urea, and the like. Urea is preferred.

2. Solvents

The hair color composition may contain one or more solvents that assist in solubilizing the dye molecule. Certain dye molecules may be less soluble in aqueous media and the solvent will assist in solubilizing the more water insoluble dyes in the aqueous composition. Suggested ranges of solvent are 0.1–30%, preferably 0.5–25%, more preferably 1–20% by weight of the total composition. Suitable solvents are volatile organic solvents such as mono and difunctional alcohols such as ethanol, isopropanol, butanol, butylene glycol, ethylene glycol, and the like. Prefereed is ethanol or isopropanol.

While the hair color compositions may have a pH spanning a wide range, it is preferable that the compositions have a pH in a range that is the gentlest to hair. The most preferred pH range is 6 to 9, more preferably from 6.5 to 8. The composition may be adjusted to the proper pH with acids or bases traditionally used for this purpose.

The composition may also contain other ingredients such as cationic hair conditioning agents, including cationic quaternary ammonium compounds, cationic silicones, and the like.

II. The Color Removing Composition

The color is removed from the hair with a composition containing a reducing agent in aqueous media. The color removing composition may be in the form of a shampoo, conditioner, or hair treatment product. In addition to the reducing agent in aqueous media, the color removing composition may contain one or more ancillary ingredients that improve the aesthetics and performance of the composition.

A. The Reducing Agent

The reducing agent used in the color removing composition is capable of disrupting the —S—S— bonds formed between the dye molecule and the hair fiber surface during the hair coloring process. A variety of reducing agents are suitable, especially those set forth above, for use in the hair color composition. Suggested ranges of reducing agent are 0.1–40%, preferably 0.5–35%, more preferably 1–30% by weight of the total composition. It may be desirable to use the same reducing agent that was used in the hair color composition, or it may be desirable to use a different reducing agent. Preferably, the reducing agent used in the color removal composition is different from the reducing agent used in the hair color composition. Most preferably, the reducing agent used in the color removing composition is sodium sulfite.

B. Aqueous Carrier

The color removal composition comprises 0.1–99%, preferably 0.5–95%, more preferably 1–80% by weight of the total composition of water.

C. Other Ingredients

In the case where the color removal composition is in the form of a shampoo, the composition typically comprises cleansing surfactants in combination with other desired ingredients in aqueous media. Shampoos typically comprise 0.1–50% of a cleansing surfactant, and 25–99% water, in addition to other desirable ingredients. If the color removal composition is in the form of a conditioner, the composition will typically be in the form of an oil and water emulsion containing about 1–99% water, 1–99% oil, and 0.1–35% of one or more cationic conditioning agents. If the hair removal composition is in the form of a treatment composition, it may an oil based composition or water and oil emulsion. Typically, a treatment composition will contain 0.1–99% water, and 0.1–99% oil, and, if desired, other treatment ingredients. The ingredients that may be used to make the various types of color removal compositions are set forth below:

1. Cleansing Surfactants

In the case where the color removal composition is a shampoo, it contains cleansing surfactants such as anionic, amphoteric, or zwitterionic surfactants. Suggested ranges of cleansing surfactant include 0.1–50%, preferably 0.5–40%, more preferably 1–35% by weight of the total composition.

(a) Anionic Surfactants

Anionic surfactants include alkyl and alkyl ether sulfates generally having the formula $ROSO_3M$ and $RO(C_2H_4O)_xSO_3M$ wherein R is alkyl or alkenyl of from about 10 to 20 carbon atoms, x is 1 to about 10 and M is a water soluble cation such as ammonium, sodium, potassium, or triethanolamine cation.

Another type of anionic surfactant which may be used in the compositions of the invention are water soluble salts of organic, sulfuric acid reaction products of the general formula:

$$R_1-SO_3-M$$

wherein $R_1$ is chosen from the group consisting of a straight or branched chain, saturated aliphatic hydrocarbon radical having from about 8 to about 24 carbon atoms, preferably 12 to about 18 carbon atoms; and M is a cation. Examples of such anionic surfactants are salts of organic sulfuric acid reaction products of hydrocarbons such as n-paraffins having 8 to 24 carbon atoms, and a sulfonating agent, such as sulfur trioxide.

Also suitable as anionic surfactants are reaction products of fatty acids esterified with isethionic acid and neutralized with sodium hydroxide. The fatty acids may be derived from coconut oil, for example.

In addition, succinates and succinimates are suitable anionic surfactants. This class includes compounds such as disodium N-octadecylsulfosuccinate; tetrasodium N-(1,2-dicarboxyethyl)-N-octadecylsulfosuccinate; and esters of sodium sulfosuccinic acid e.g. the dihexyl ester of sodium sulfosuccinic acid, the dioctyl ester of sodium sulfosuccinic acid, and the like.

Other suitable anionic surfactants include olefin sulfonates having about 12 to 24 carbon atoms. The term "olefin sulfonate" means a compound that can be produced by sulfonation of an alpha olefin by means of uncomplexed sulfur trioxide, followed by neutralization of the acid reaction mixture in conditions such that any sultones which have been formed in the reaction are hydrolyzed to give the corresponding hydroxy-alkanesulfonates. The alpha-olefin from which the olefin sulfonate is derived is a mono-olefin having about 12 to 24 carbon atoms, preferably about 14 to 16 carbon atoms.

Other classes of suitable anionic organic surfactants are the beta-alkoxy alkane sulfonates or water soluble soaps thereof such as the salts of $C_{10-20}$ fatty acids, for example coconut and tallow based soaps. Preferred salts are ammonium, potassium, and sodium salts.

Still another class of anionic surfactants include N-acyl amino acid surfactants and salts thereof (alkali, alkaline earth, and ammonium salts) having the formula:

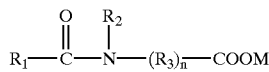

wherein $R_1$ is a $C_{8-24}$ alkyl or alkenyl radical, preferably $C_{10-18}$, $R_2$ is H, $C_{1-4}$ alkyl, phenyl, or $-CH_2COOM$; $R_3$ is $CX_2-$ or $C_{1-2}$ alkoxy, wherein each X independently is H or a $C_{1-6}$ alkyl or alkylester, n is from 1 to 4, and M is H or a salt forming cation as described above. Examples of such surfactants are the N-acyl sarcosinates, including lauroyl sarcosinate, myristoyl sarcosinate, cocoyl sarcosinate, and oleoyl sarcosinate, preferably in sodium or potassium forms.

(b) Nonionic Surfactants

The composition can contain one or more nonionic surfactants in lieu of, or in addition to, the anionic surfactant. Nonionic surfactants are generally compounds produced by the condensation of alkylene oxide groups with a hydrophobic compound.

Classes of nonionic surfactants are:

(a) Long chain dialkyl sulfoxides containing one short chain alkyl or hydroxy alkyl radical of from about 1 to 3 carbon atoms and one long hydrophobic chain which may be an alkyl, alkenyl, hydroxyalkyl, or ketoalkyl radical containing from about 8 to 20 carbon atoms, from 0 to 10 ethylene oxide moieties, and 0 or 1 glyceryl moiety.

(b) Polysorbates, such as sucrose esters of fatty acids. Examples of such materials include sucrose cocoate, sucrose behenate, and so on.

(c) Polyethylene oxide condensates of alkyl phenols, for example the condensation products of alkyl phenols having an alkyl group of 6 to 20 carbon atoms with ethylene oxide being present in amounts of about 10 to 60 moles of ethylene oxide per mole of alkyl phenol.

(d) Condensation products of ethylene oxide with the reaction product of propylene oxide and ethylene diamine.

(e) Condensation products of aliphatic alcohols having 8 to 18 carbon atoms with ethylene oxide, for example a coconut alcohol/ethylene oxide condensate having 10 to 30 moles of ethylene oxide per mole of coconut alcohol, the coconut alcohol fraction having 10 to 14 carbon atoms.

(f) Long chain tertiary amine oxides such as those corresponding to the general formula:

$$R_1R_2R_3NO$$

wherein $R_1$ contains an alkyl, alkenyl or monohydroxyalkyl radical ranging from about 8 to 18 carbon atoms in length, from 0 to about 10 ethylene oxide moieties, and from 0 to about 1 moiety and $R_2$ and $R_3$ are each alkyl or monohydroxyalkyl groups containing from about 1 to about 3 carbon atoms.

(g) Long chain tertiary phosphine oxides corresponding to the general formula:

$$RR_1R_2PO$$

wherein R contains an alkyl, alkenyl, or monohydroxyalkyl radical having 8 to 18 carbon atoms, from 0–10 ethylene oxide moieties and 0 or 1 glyceryl moiety, and $R_2$ and $R_3$ are each alkyl or monohydroxyalkyl group containing from about 1 to 3 carbon atoms.

(h) Alkyl polysaccharides having a hydrophobic group of 6 to 30, preferably 10, carbon atoms and a polysaccharide group such as glucose, galactose, etc. Suitable alkyl polysaccharides are octyl, nonydecyl, undecyldodecyl, tridecyl, tetradecyl, pentadecyl, hexadecyl, heptadecyl, and octadecyl, di-, tri-, tetra-, penta-, and hexaglucosides, galactosides, lactosides, glucoses, fructosides, fructoses, and so on.

(i) Polyethylene glycol (PEG) glyceryl fatty esters, having the formula $$RC(O)OCH_2CH(OH)CH_2(OCH_2CH_2)_nOH$$

wherein n is 5–200 and RC(O)— is a hydrocarbylcarbonyl group wherein R is preferably an aliphatic radical having 7 to 19 carbon atoms.

(j) Other nonionic surfactants that may be used include $C_{10-18}$ alkyl($C_{1-6}$)polyhydroxy fatty acid amides such as $C_{12-18}$ methylglucamides, N-alkoxy polyhydroxy fatty acid amides, N-propyl through N-hexyl $C_{12-18}$ glucamides and so on.

(c) Amphoteric Surfactants

Amphoteric surfactants that can be used in the compositions of the invention are generally described as derivatives of aliphatic secondary or tertiary amines wherein one aliphatic radical is a straight or branched chain alkyl of 8 to 18 carbon atoms and the other aliphatic radical contains an anionic group such as carboxy, sulfonate, sulfate, phosphate, or phosphonate.

Suitable amphoteric surfactants may have the following general formula:

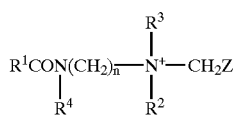

wherein $R^1$ is $C_{8-22}$ alkyl or alkenyl, preferably $C_{12-16}$; $R^2$ is hydrogen or $CH_2CO_2M$, $R^3$ is $CH_2CH_2OH$ or $CH_2CH_2OCH_2CHCOOM$; $R^4$ is hydrogen, $CH_2CH_2OH$, or $CH_2CH_2OCH_2CH_2COOM$, Z is $CO_2M$ or $CH_2CO_2M$, n is 2 or 3, preferably 2, M is hydrogen or a cation such as an alkali metal, alkaline earth metal, ammonium, or alkanol ammonium cation. Examples of such materials are marketed under the tradename MIRANOL, by Miranol, Inc.

Also suitable amphoteric surfactants are monocarboxylates or dicarboxylates such as cocamphocarboxypropionate, cocoamphocarboxypropionic acid, cocamphocarboxyglycinate, and cocoamphoacetate Other types of amphoteric surfactants include aminoalkanoates of the formula

or iminodialkanoates of the formula:

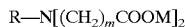

and mixtures thereof; wherein n and m are 1 to 4, R is $C_{8-22}$ alkyl or alkenyl, and M is hydrogen, alkali metal, alkaline earth metal, ammonium or alkanolammonium. Examples of such amphoteric surfactants include n-alkylaminopropionates and n-alkyliminodipropionates, which are sold under the trade name MIRATAINE by Miranol, Inc. or DERIPHAT by Henkel, for example N-lauryl-beta-amino propionic acid, N-lauryl-beta-iminodipropionic acid, or mixtures thereof.

(d) Zwitterionic Surfactants

Zwitterionic surfactants are also suitable for use in the compositions of the invention. The general formula for such surfactants is:

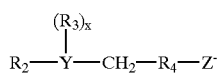

wherein $R_2$ contains an alkyl alkenyl or hydroxy alkyl radical of from about 8 to about 18 carbon atoms, from 0 to about 10 ethylene oxide moieties and 0 or 1 glyceryl moiety; Y is selected from the group consisting of nitrogen, phosphorus, and sulfur atoms; $R_3$ is an alkyl or monohydroxyalkyl group containing about 1 to 3 carbon atoms; X is 1 when Y is a sulfur atom, and 2 when Y is a nitrogen or phosphorus atom: $R_4$ is an alkylene or hydroxyalkylene of from about 1 to about 4 carbon atoms, and Z is a radical selected from the group consisting of carboxylate, sulfonate, sulfate, phosphonate, and phosphate groups.

Zwitterionics include betaines, for example higher alkyl betaines such as coco dimethyl carboxymethyl betaine, lauryl dimethyl carboxymethyl betaine, lauryl dimethyl alphacarboxyethyl betaine, cetyl dimethyl carboxymethyl betaine, lauryl bis-(2-hydroxyethyl)carboxymethyl-betaine, stearyl bis-(2-hydroxypropyl)carboxymethyl betaine, oleyl dimethyl gamma-carboxylethyl betaine, and mixtures thereof. Also suitable are sulfo- and amido- betaines such as coco dimethyl sulfopropyl betaine, stearyl dimethyl sulfopropyl betaine, and the like.

2. Hair Conditioning Agents

Color removal compositions in the shampoo conditioner, or treatment composition form may contain 0.01–15%, preferably 0.05–10%, preferably 0.10–8% of a cationic conditioning agent which is a cationic polymer, a quaternary ammonium salt or the salt of a fatty amine. Quaternary ammonium salts have the formula:

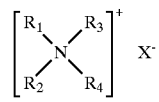

wherein $R_1$ is hydrogen, an aliphatic group of 1 to 22 carbon atoms, or aromatic, aryl, or alkaryl group having 12 to 22 carbon atoms; $R_2$ is an aliphatic group having 1–22 carbon atoms; $R_3$ and $R_4$ are each alkyl groups of from 1 to 3 carbon atoms, and X is an anion selected from halogen, acetate, phosphate, nitrate and methyl sulfate radicals. The aliphatic groups may contain, in addition to carbon and hydrogen atoms, ether linkages as well as amido groups.

Suitable quaternary ammonium compounds may be mono-long chain alkyl, di-long chain alkyl, tri-long chain alkyl, and the like. Examples of such quaternary ammonium salts include behenalkonium chloride, behentrimonium chloride, behentrimonium methosulfate, benzalkonium chloride, benzethonium chloride, benzyl triethyl ammonium chloride, cetalkonium-chloride, cetrimonium chloride, cetrimonium bromide, cetrimonium methosulfate, cetrimonium tosylate, cetylpyridinium chloride, dibehenyl/diarachidyl dimonium chloride, dibehenyldimonium chloride, dibehenyldimonium methosulfate, dicapryl/dicaprylyl dimonium chloride, dicetyldimonium chloride, and mixtures thereof.

Other quarternary ammonium salts useful as the cationic conditioning agent are compounds of the general formula:

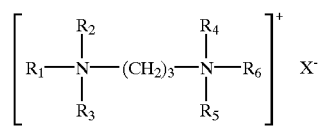

wherein $R_1$ is an aliphatic group having 16 to 22 carbon atoms, $R_2$, $R_3$, $R_4$, $R_5$, and $R_6$ are the same or different and are selected from H and alkyls having 1 to 4 carbon atoms and X is an anion as above defined.

Also, quaternary imidazolinium salts having the following general formula are also suitable:

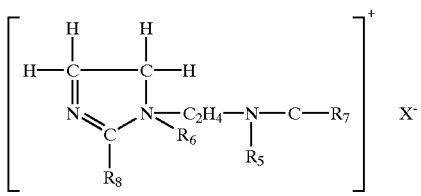

wherein $R_5$ is hydrogen or a $C_{1-4}$ alkyl; $R_6$ is a $C_{1-4}$ alkyl; $R_7$ is a $C_{8-22}$ alkyl; and R8 is hydrogen, or a $C_{1-22}$ alkyl; and X is an anion as defined above.

Also suitable as the cationic hair conditioning agent are salts of fatty primary, secondary, or tertiary amines, wherein the substituted groups have 12 to 22 carbon atoms. Examples of such amines include dimethyl stearamine, dimethyl soyamine, stearylamine, myristylamine, tridecylamine, ethyl stearamine, and so on.

Also suitable as the cationic conditioning agent are cationic polymers such as:
(a) Quaternary derivatives of cellulose ethers such as polymers sold under the tradename JR-125, JR400, JR-30M. Preferred is Polyquaternium 10, which is a polymeric quaternary ammonium salt of hydroxyethyl cellulose reacted with a trimethyl ammonium subsituted epoxide.
(b) Copolymers of vinylpyrrolidone having monomer units of the formula:

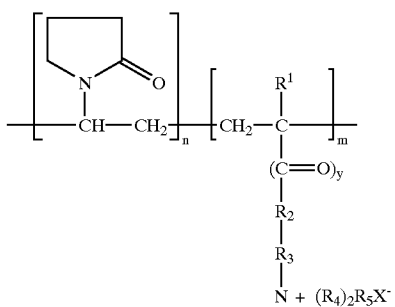

wherein
$R^1$ is hydrogen or methyl, preferably methyl;
y is 0 or 1, preferably 1
$R^2$ is 0 or NH, preferably NH;
$R^3$ is $C_xH_{2x}$ where x is 2 to 18, or —$CH_2$—CHOH—$CH_2$, preferably $C_xH_{2x}$ where x is 2;
$R^4$ is methyl, ethyl, phenyl, or $C_{1-4}$ substituted phenyl, preferably methyl; and
$R^5$ is methyl or ethyl, preferably methyl.

Preferred are compounds of the above formula wherein y is 1, $R^2$ is NH, $R^3$ is $CH_2CH_2$, $R^4$ is methyl, and $R^5$ is methyl. Such compounds are known by the CTFA designation Polyquaternium 28.
(c) Homopolymer of dimethyldiallylammonium chloride, or copolymer of dimethyldiallylammonium chloride and acrylamide. Such compounds are sold under the tradename MERQUAT™ by Merck.
(d) Homopolymers or copolymers derived from acrylic or methacrylic acid wherein the monomer units are selected from the group consisting of acrylamide, methylacrylamide, diacetone-acrylamide, acrylamide or methacrylamide substituted on the nitrogen by lower alkyl, alkyl esters of acrylic acid and methacrylic acid, vinylpyrrolidone, and vinyl esters.

Examples of cationic polymers that can be used in the compositions of the invention are the cationic polymers disclosed in U.S. Pat. Nos. 5,240,450 and 5,573,709, which are hereby incorporated by reference.

3. Humectants

Color removal compositions in the form of shampoos, conditioners, or treatment compositions may additionally contain humectants, which provide moisturizing and swelling properties to the hair. Suggested ranges of humectant are 0.1–30%, preferably 0.5–25%, more preferably 1–20% by weight of the total composition. Suitable humectants are those listed above for use in the hair color composition.

4. Protein Conditioning Agents

Color removal compositions in the form of shampoos, conditioners, or treatment compositions may contain about 0.001–10% preferably 0.005–8%, more preferably 0.01–5% by weight of the total composition of protein conditioning agents, which further condition hair. Examples of protein conditioning agents are preferably hydrolysates such as hydrolyzed silk, hydrolyzed wheat protein, hydrolyzed wheat protein/wheat oligosaccharides, hydrolyzed marine collagen, wheat amino acids, PVP/hydrolyzed wheat protein copolymer (which is a copolymer of polyvinylpyrrolidone and hydrolyzed wheat protein). Particularly preferred is hydrolyzed silk.

Preferred color removal compositions are shampoos.

C. The Method

The hair color composition used in the method of the invention is functional as is, and does not require mixing with an activating composition immediately prior to use as do the typical oxidative hair dyes currently used today. The hair color composition may be sold by itself in a single container, or in a two pack kit with the hair color composition in one container and the color removal composition in a second container. If desired, the hair color composition and color removal composition may be sold in a multi pack kit that has containers of other hair care compositions such as shampoo or conditioner which are designed to be used between the hair coloring and hair color removal steps. Because the hair color composition used in the method of the invention does not require activation, it has a longer shelf life that traditional oxidative hair color. The composition may be opened and re-used, possibly even until the composition has been used up. This results in considerable savings. Consumers who have short hair, or those who only wish to touch up their hair color, need only use a small amount. The rest of the composition can be stored for further use when needed. In contrast, the traditional oxidative dyes must be used quickly after mixing the hair color with the activating composition, because the dye quickly loses its efficacy.

The desired amount of the hair color composition is applied to the hair and allowed to remain for an amount of time necessary to cause coloration of the hair, generally 5 to 65 minutes, preferably 10 to 45 minutes. As previously discussed, the reducing agent present in the hair color composition reacts with the —S—S— bonds on the hair fiber surface to cause formation of —SH groups on the hair fiber surface. The dye molecule, which contains chemical groups capable of chemically reacting with the —SH groups formed on the hair by the reducing agent, will react with the —SH groups to form a bond between the hair dye molecule and the hair fiber surface, which causes the hair color to become affixed to the hair fiber surface via formation of disulfide, or —S—S— bonds. This reaction occurs at ambient temperature upon exposure to the air. The oxygen in air causes oxidation of the —SH bonds to form —S—S— bonds in a period of time ranging from ten to sixty five minutes. After the appropriate period of time, the hair color composition is rinsed from the hair with water and the hair allowed to dry. The dye molecule is thereby affixed to the hair by covalent bonding for as long as the user cares to leave the color on the hair. The color applied to hair in this manner is sufficiently "permanent" to remain on the hair for extended periods of time, up to six months, if desired. On the other hand, the color can be removed from hair when desired, by application of the color removal composition. Preferably, the user will wear the color for one to forty five days. After this, the user may elect to remove the color with the color removal composition, then color the hair again.

At the desired point in time, the user may remove the color from the hair by application of the color removal composition. This composition is applied to the hair for a period of 5 to 65 minutes. The color removal composition contains a reducing agent that is capable of reacting with the —S—S— bonds formed between the hair dye molecule and hair fiber surface, which disrupts the —S—S— bonds and causes the hair dye molecule to become disassociated from the hair, and the formation of —SH groups on the hair fiber surface. The color removal composition is left on the hair for a period of time ranging from five to sixty five minutes. The color removal composition is then rinsed from the hair with warm water and the hair dried. The —SH groups remaining on the hair after disruption of the dye molecule from the hair fiber surface will reform —S—S— bonds upon exposure to air.

The method of the invention provides a hair color that can be bonded to the hair fiber surface, and removed from hair when desired by application of a composition that is gentle to the hair. The dye molecule does not enter into the hair shaft or otherwise compromise the integrity of the hair, but rather, coats the hair surface. Thus, it tends to be gentler on the hair. The color removal composition, similarly, contains only reducing agents which are not harsh when applied to hair.

The invention will be further described in connection with the following examples which are set forth for the purposes of illustration only.

EXAMPLE 1

A hair color composition is made according to the following formula:

|   | w/w % |
|---|---|
| Glyceryl-thioglycollate (reducing agent) | 4.00 |
| Urea | 10.00 |
| Polymeric dye compound* | 8.40 |
| Ethanol | 8.43 |
| Acetic acid QS to pH 7.00 | |
| Water QS to 100 | |

*the polymeric dye compound had the following formula:

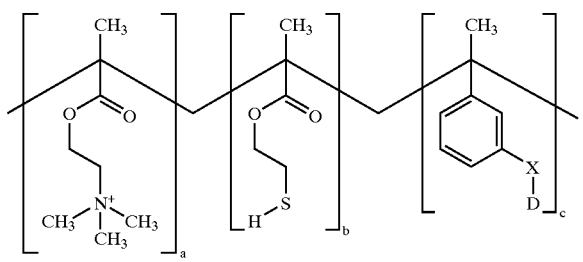

wherein a:b:c is 10:9:1 respectively, X is —(CH$_3$)$_2$CNHCO$_2$—, and D is

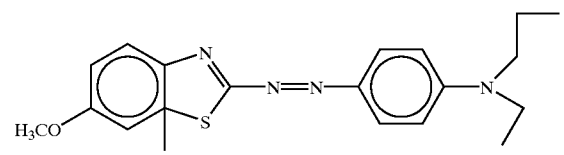

The hair color composition is made by combining the ingredients and mixing well. The composition is applied to gray hair tresses and left on the hair for about 30 minutes and rinsed well with water. The hair was dyed an intense blue color.

Thereafter, the hair tresses are subjected to ten shampoos with a standard shampoo composition comprised of an anionic surfactant in aqueous media. The color remains fast and no significant color fading is observed.

EXAMPLE 2

A color removing shampoo in accordance with the invention is made as follows:

|   | w/w % |   |
|---|---|---|
| Sodium lauryl sulfate (30% aqueous solution) | 1.5 | |
| Sodium laureth sulfate (28% aqueous solution) | 0.7 | |
| Lauramide DEA | 0.15 | |
| Sodium sulfite | 10.00 | (reducing agent) |
| Fragrance | 0.10 | |
| Methyl paraben | 0.10 | |
| Propyl paraben | 0.05 | |
| Guar hydroxypropyl trimonium chloride | 0.10 | |
| Urea | 10.00 | |
| Glycol stearate | 0.01 | |
| Myristic acid | 0.01 | |
| Citric acid | 0.01 | |
| Hydrolyzed silk | 0.01 | |
| Cocamidopropyl betaine (35% aqueous solution) | 0.35 | |
| Dimethicone copolyol | 0.03 | |
| Glycerin (96% aqueous solution) | 0.01 | |
| Trisodium HEDTA | 0.01 | |
| Methylchloroisothiazolinone/ methylisothiazolinone | 0.04 | |
| Water QS 100 | | |

The shampoo composition is made by combining the ingredients and mixing well. The hair tress dyed in Example 1 is treated with the above shampoo composition by applying the composition to the hair for fifteen minutes, then rinsing with water. More than 90% of the intense blue color is removed from the hair.

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

We claim:

1. A method for coloring hair and removing the color from the hair when desired, comprising the steps of:
   (a) coloring the hair with an aqueous hair color composition comprising, in combination: (i) a reducing agent capable of reducing the —S—S— bonds on the hair fiber surface to form reactive —SH groups; and (ii) a dye molecule containing at least one (a) chromophore, and at least one (b) free reactive group selected from the group consisting of —SH, thiouronium salts, bunte salts, and mixtures thereof, which dye molecule, upon contact with the hair, reacts with the —SH groups on the hair fiber surface to form —S—S— bonds between the dye molecule and the hair fiber surface when the hair color composition is applied to the hair at ambient conditions;

(b) wearing the colored hair for the desired period of time;

(c) removing the color applied in step (a) from the hair by contacting the hair with an aqueous based shampoo color removal composition containing a cleansing surfactant and a reducing agent capable of disrupting the —S—S— bonds between the dye molecule and the hair fiber surface to cause the dye molecule to become disassociated from the hair fiber.

2. The method of claim 1 wherein the cleansing surfactant in the aqueous based shampoo color removal composition is a anionic surfactant.

3. The method of claim 2 wherein the anionic surfactant is an alkyl sulfate or alkyl ether sulfate.

4. The method of claim 1 wherein the chromophore is an Acid dye.

5. The method of claim 1 wherein the chromophore is a Basic dye.

6. The method of claim 1 wherein the hair color composition comprises, by weight of the total composition:
   1–30% of the dye molecule wherein the chromophore is selected from the group consisting of Acid dye, Basic dye, Disperse dye, and mixtures thereof,
   0.1–25% of the reducing agent, and
   1–99% water.

7. The method of claim 6 wherein the hair color composition has a pH ranging from about 5 to 8.

8. The method of claim 1 wherein the dye molecule comprises an acrylate or methacrylate polymer.

9. The method of claim 6 wherein the hair color composition additionally comprises 0.1–20% of a humectant.

10. The method of claim 6 wherein the hair color composition additionally comprises 0.1–20% of a volatile solvent.

11. The method of claim 10 wherein the volatile solvent is alcohol.

12. The method of claim 1 wherein the dye molecule is a polymer having the general formula:

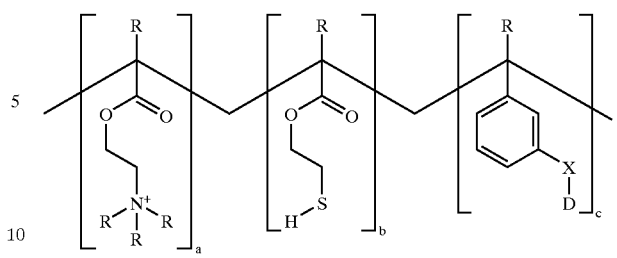

wherein:
a, b, and c are each independently integers ranging from 1 to 100,000;
Each R is independently H, or $C_{1-6}$ alkyl,
X is a linking group selected from the group consisting of —$C_mH_{2m}$NR'—, —NR'—, —NR'C=O—, —C(O)NR'—, —NR'SO_2—, SO_2NR'—, —$C_mH_{2m}$NR'CO_2, or $C_mH_{2m}CO_2$; wherein m is an integer from 0 to 1,000 and R' is SH; and
D is a chromophore that absorbs visible light.

13. The method of claim 1 wherein the color removal composition comprises, by weight of the total composition:
   5–40% of the reducing agent,
   0.1–50% cleansing surfactant; and
   1–99% water.

14. The method of claim 13 wherein the color removal composition further comprises a hair conditioning agent selected from the group consisting of cationic surfactant, cationic polymer, and mixtures thereof.

15. The method of claim 14 wherein the shampoo comprises, by weight of the total composition:
   0.5–20% of a cleansing surfactant,
   5–40% of the reducing agent,
   0.01–15% cationic conditioning agent; and
   1–99% water.

16. The method of claim 15 wherein the shampoo further comprises 0.1–30% of a humectant.

17. The method of claim 16 wherein the color removal composition is left on the hair for 10 to 60 minutes to remove color from the hair.

18. The method of claim 13 wherein the reducing agent is sodium sulfite.

19. A method for removing dye bonded to the hair fibers via an —S—S— linkage, comprising applying to the hair an aqueous based color removal composition containing a reducing agent capable of disrupting the —S—S— bonds between the dye and hair fiber surface.

20. The method of claim 19 wherein the aqueous based color removal composition is a shampoo.

* * * * *